United States Patent [19]

Chapura

[11] 3,932,613
[45] Jan. 13, 1976

[54] METHOD OF PREVENTING LEAKAGE FROM BODY ORIFICES WHEN UTILIZING SUPPOSITORIES AS A SOURCE OF MEDICATION

[75] Inventor: Francis B. Chapura, Norwich, N.Y.

[73] Assignee: Morton-Norwich Products, Inc., Norwich, N.Y.

[22] Filed: Aug. 20, 1973

[21] Appl. No.: 389,462

[52] U.S. Cl.................................. 424/78; 424/127
[51] Int. Cl.² ......................................... A61K 31/74
[58] Field of Search .............. 424/127, 307, 342, 78

[56] References Cited
UNITED STATES PATENTS

| 2,975,099 | 3/1961 | Goyan et al. | 424/181 |
| 3,234,091 | 2/1966 | Lang et al. | 424/14 |

Primary Examiner—V. D. Turner
Attorney, Agent, or Firm—Anthony J. Franze

[57] ABSTRACT

This invention relates to a non-leaking suppository base.

1 Claim, No Drawings

METHOD OF PREVENTING LEAKAGE FROM BODY ORIFICES WHEN UTILIZING SUPPOSITORIES AS A SOURCE OF MEDICATION

A suppository base that will not leak from the body orifice into which it is inserted is of significant value in administration and application of medicinals, cosmetics and other like ingredients. This invention is concerned with the preparation of such a base by incorporating therein, substances having thixotropic properties. Suppositories, although a widely used means for delivery of medication, have several glaring faults which detract from their usefulness. When suppositories melt or dissolve in the body fluids upon insertion into the body orifice, the formed liquid oftentimes flows from the body orifice. Furthermore, this leakage may occure before the substance intended to be administered has sufficient time to produce the desired effect. This leakage is undesirable as an esthetic and as a therapeutic consideration, for beside the spoilage of garments, the leakage carries with it the intended substance to be delivered into the orifice.

It has been found that addition of a substance to a suppository base which will produce a thixotropic effect in the base upon melting, or upon dissolving in the body fluids will eliminate or reduce this undesirable characteristic of leakage in these suppositories.

A suppository which is designed to melt in the body or dissolve in body fluids, when the proper thixotropicity producing material is added, will continue to melt or dissolve at body temperature and spread until it forms a thin film. When the force required to spread the film of medication is equivalent to the yield value of the thixotropic suppository base, spreading will stop. The yield value of a thixotropic substance is that force below which the substance will not flow. The proper thixotropic substance will not significantly affect the melting point or dissolution of the other compounds.

This suppository base which will not leak from the body orifice, is capable of being molded due to the presence of its wax and wax-like components. The major proportion of the base consists of ingredients that are polymers of ethylene oxide, more commonly referred to as "polyethylene glycols". Using such substances, one can tailor the base to meet any particular need with regard to melting point, dissolution rate, or precompensation of the melting point lowering effect of active ingredients which might be added. These polymers are also selected because of their miscibility with aqueous secretions of the mucus membranes which will assist in the prevention of leakage.

The human body having a temperature of 37°C. prescribes the selection of polyethylene glycols which will permit the suppository base to melt or readily dissolve at about that temperature. Combinations of two or more polyethylene glycols which will impart the ability of the base to melt or dissolve at 37°C. may be used. The polyethylene glycols or polymers of ethylene oxide referred to herein are represented by the general formula $HOCH_2(CH_2OCH_2)_nCH_2OH$.

In the practice of this invention it has been found that a combination of Polyethylene Glycol 300 whose average molecular weight is 285 to 315 and Polyethylene Glycol 1000 whose average molecular weight is not less than 950 and not more than 1050 to be particularly efficacious as the major components of the base.

The thixotropic substances which have been selected for incorporation in the polyethylene glycol base are marketed under the trademarks CAB-O-SIL and CARBOPOL 940. CAB-O-SIL is marketed by Godfrey L. Cabot, Inc. of Boston, Massachusetts and may be described as an amorphus silica of high purity obtained from the gaseous phase, with a particle size of about 15 mu. and a surface area of 175–200 $m_2/g$. CARBOPOL 940 is a product of B. F. Goodrich Chemical Company and may be described as an extremely high molecular weight carboxyvinyl polymer resin having the generic designation of "carboxypolymethylene."

The addition of such thixotropic substances will prevent the free flow of the liquid which results from the dissolution and melting of the suppository base.

In order to illustrate this new non-leaking suppository base, the following specific formulations embodying this invention are provided:

EXAMPLE I

|  | Parts By Weight |
|---|---|
| Polyethylene Gylcol 1000 | 91.43 |
| Polyethylene Glycol 300 | 2.97 |
| Polyoxyethylene Palmitate | 0.50 |
| Methyl Paraben | 0.10 |
| Cab-O-Sil | 5.00 |

At a temperature range of 50° – 55°C. the polyethylene glycol 1000 and polyoxyethylene palmitate are melted together. The polyoxethylene palmitate is a palmitic ester of ethylene oxide containing approximately 20 oxyethylene units. To this mixture is added the polyethylene glycol 300 and methyl paraben under conditions of constant stirring until a homogeneous liquid is obtained. The "CAB-O-SIL" is slowly added and constantly stirred until thoroughly incorporated in the mixture.

The mixture is poured into suitable molds and allowed to harden.

EXAMPLE II

|  | Parts by Weight |
|---|---|
| Polyethylene Glycol 1000 | 94.93 |
| Polyethylene Glycol 300 | 2.97 |
| Polyoxyethylene Palmitate | 0.50 |
| Methyl Paraben | 0.10 |
| Carbopol 940 | 1.50 |

At a temperature range of 50° – 55°C. the polyethylene glycol 1000 and polyoxyethylene palmitate are melted together. The polyethylene glycol 300 and methyl paraben are added to the melted mixture and stirred. The "CARBOPOL 940" is added slowly under conditions of constant stirring. The mixture is poured into suitable molds and allowed to harden.

What is claimed is:

1. A suppository base consisting of from 91 to 95 parts of a polyethylene glycol having an average molecular weight of about 1000; three parts of a polyethylene glycol having an average molecular weight of 300; one-half part of polyoxyethylene palmitate containing about 20 oxyethylene units; and from one and one-half to five and one half parts of a member selected from the group consisting of amorphous silica and carboxyvinyl polymer resin.

* * * * *